US008658695B2

(12) United States Patent
Bay et al.

(10) Patent No.: US 8,658,695 B2
(45) Date of Patent: *Feb. 25, 2014

(54) DISODIUM SALTS, MONOHYDRATES, AND ETHANOL SOLVATES FOR DELIVERING ACTIVE AGENTS

(75) Inventors: William Elliott Bay, Ridgefield, CT (US); Rajesh K. Agarwal, Yorktown Heights, NY (US); Kiran Chaudhary, West Nyack, NY (US); Shingai Majuru, Brewster, NY (US); Michael M. Goldberg, Englewood, NJ (US); JoAnne P. Corvino, Harrison, NY (US); Moise Azria, Basel (CH); Joseph Ault, Blairstown, NJ (US); Simon D. Bateman, Randolph, NJ (US); Subash Patel, Somerville, NJ (US); Joseph Sikora, Succasunna, NJ (US); Rebecca F. Yang, Randolph, NJ (US); Joseph Zielinski, Florham Park, NJ (US)

(73) Assignees: Emisphere Technologies, Inc., Roseland, NJ (US); Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,310

(22) Filed: May 25, 2012

(65) Prior Publication Data
US 2012/0264834 A1 Oct. 18, 2012

Related U.S. Application Data

(63) Continuation of application No. 13/053,641, filed on Mar. 22, 2011, now Pat. No. 8,207,227, which is a continuation of application No. 12/642,508, filed on Dec. 18, 2009, now Pat. No. 8,003,697, which is a continuation of application No. 12/111,750, filed on Apr. 29, 2008, now Pat. No. 7,659,311, which is a continuation of application No. 10/615,213, filed on Jul. 7, 2003, now Pat. No. 7,384,982, which is a continuation of application No. 09/962,794, filed on Sep. 24, 2001, now abandoned, which is a continuation of application No. PCT/US00/09390, filed on Apr. 5, 2000.

(60) Provisional application No. 60/127,754, filed on Apr. 5, 1999, provisional application No. 60/186,143, filed on Mar. 1, 2000, provisional application No. 60/186,142, filed on Mar. 1, 2000, provisional application No. 60/191,286, filed on Mar. 21, 2000.

(51) Int. Cl.
*A61K 31/195* (2006.01)
*C07C 229/00* (2006.01)

(52) U.S. Cl.
USPC .......................... 514/563; 562/444; 562/450

(58) Field of Classification Search
USPC .................. 514/563; 562/444, 450
See application file for complete search history.

(56) References Cited

U.S. PATENT DOCUMENTS

| 3,795,739 A | 3/1974 | Birkmayer et al. |
| 3,939,253 A | 2/1976 | Bodor et al. |
| 4,035,507 A | 7/1977 | Bodor et al. |
| 4,061,466 A | 12/1977 | Sjoholm et al. |
| 4,147,767 A | 4/1979 | Yapel, Jr. |
| 4,207,341 A | 6/1980 | Hubner et al. |
| 4,221,815 A | 9/1980 | Weyer et al. |
| 4,238,506 A | 12/1980 | Stach et al. |
| 4,239,754 A | 12/1980 | Sache et al. |
| 4,393,192 A | 7/1983 | Curatolo et al. |
| 4,442,090 A | 4/1984 | Kakeya et al. |
| 4,462,991 A | 7/1984 | Higuchi et al. |
| 4,499,299 A | 2/1985 | Bernstein et al. |
| 4,654,327 A | 3/1987 | Teng |
| 4,656,161 A | 4/1987 | Herr |
| 4,692,433 A | 9/1987 | Hostetler et al. |
| 4,757,066 A | 7/1988 | Shiokari et al. |
| 4,835,312 A | 5/1989 | Itoh et al. |
| 4,873,087 A | 10/1989 | Morishita et al. |
| 4,878,942 A | 11/1989 | Motegi et al. |
| 4,898,729 A | 2/1990 | Miller et al. |
| 4,900,730 A | 2/1990 | Miyauchi |
| 4,927,928 A | 5/1990 | Shroot et al. |
| 5,066,487 A | 11/1991 | Morelle et al. |

(Continued)

FOREIGN PATENT DOCUMENTS

| CA | 1234561 A1 | 3/1988 |
| EP | 0036145 A1 | 9/1981 |

(Continued)

OTHER PUBLICATIONS

Gonze, Mark D., et al., Orally Administered Heparin with a Carrier Agent is Therapeutic for Deep Venous Thrombosis Treatment, Vascular. pp. 335-337, 2000.
Amino Yusuke et al. Chem Pharm Bull 36 pp. 4426-4434 (1998).
Aug. 1, 2000 International Search Report issued in connection with PCT Application No. PCT/US00/09390.
Baughman, R. et al., Circulation (1998), 98 (16) 1610-1615.
Brayden, D. et al. "Heparin Absorption across the intestin: Effects of Sodium N-[8-2hydorxybenzoyl)Amino] Caprylate in rat in situ intestinal instillations ind in Caco-2 monolayers" Pharmaceutical Research vol. 14(12) 1772-1779 (1997).

(Continued)

*Primary Examiner* — Taylor Victor Oh
(74) *Attorney, Agent, or Firm* — Blank Rome LLP

(57) ABSTRACT

The inventors have discovered that the disodium salt of certain delivery agents has surprisingly greater efficacy for delivering active agents than the corresponding monosodium salt. Furthermore, the inventors have discovered that the disodium salts of these delivery agents form solvates with ethanol and hydrates with water. Preferred delivery agents include, but are not limited to, N-(5-chlorosalicyloyl)-8-aminocaprylic acid (5-CNAC), N-(10-[2-hydroxybenzoyl]amino)decanoic acid (SNAD), and sodium N-(8-[2-hydroxybenzoyl]amino)caprylate (SNAC). The invention also provides methods of preparing the disodium salt, ethanol solvate, and hydrate and compositions containing the disodium salt, ethanol solvate, and/or hydrate.

14 Claims, No Drawings

(56) References Cited

U.S. PATENT DOCUMENTS

| | | |
|---|---|---|
| 5,352,461 A | 10/1994 | Feldstein et al. |
| 5,447,728 A | 9/1995 | Milstein et al. |
| 5,451,410 A | 9/1995 | Milstein et al. |
| 5,541,155 A | 7/1996 | Leone-Bay et al. |
| 5,629,020 A | 5/1997 | Leone-Bay et al. |
| 5,643,957 A | 7/1997 | Leone-Bay et al. |
| 5,650,386 A | 7/1997 | Leone-Bay et al. |
| 5,665,700 A | 9/1997 | Cho et al. |
| 5,705,529 A | 1/1998 | Matyus et al. |
| 5,709,861 A | 1/1998 | Santiago et al. |
| 5,714,167 A | 2/1998 | Milstein et al. |
| 5,750,147 A | 5/1998 | Kantor |
| 5,766,633 A | 6/1998 | Milstein et al. |
| 5,773,647 A | 6/1998 | Leone-Bay et al. |
| RE35,862 E | 7/1998 | Steiner et al. |
| 5,776,888 A | 7/1998 | Leone-Bay et al. |
| 5,792,451 A | 8/1998 | Sarubbi et al. |
| 5,804,688 A | 9/1998 | Leone-Bay et al. |
| 5,811,127 A | 9/1998 | Milstein et al. |
| 5,863,944 A | 1/1999 | Leone-Bay et al. |
| 5,866,536 A | 2/1999 | Leone-Bay et al. |
| 5,876,710 A | 3/1999 | Leone-Bay et al. |
| 5,879,681 A | 3/1999 | Leone-Bay et al. |
| 5,939,381 A | 8/1999 | Leone-Bay et al. |
| 5,958,457 A | 9/1999 | Santiago et al. |
| 5,965,121 A | 10/1999 | Leone-Bay et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,051,258 A | 4/2000 | Kantor |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,071,538 A | 6/2000 | Milstein et al. |
| 6,090,958 A | 7/2000 | Leone-Bay et al. |
| 6,099,856 A | 8/2000 | Milstein et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,313,088 B1 | 11/2001 | Leone-Bay et al. |
| 6,344,213 B1 | 2/2002 | Leone-Bay et al. |
| 6,346,242 B1 | 2/2002 | Leone-Bay et al. |
| 7,049,283 B2 | 5/2006 | Ault et al. |
| 7,659,311 B2 | 2/2010 | Bay et al. |
| 2010/0099621 A1 | 4/2010 | Bay et al. |

FOREIGN PATENT DOCUMENTS

| | | |
|---|---|---|
| EP | 0225189 A2 | 6/1987 |
| EP | 226223 A2 | 6/1987 |
| EP | 0365183 A1 | 4/1990 |
| EP | 369853 A1 | 5/1990 |
| EP | 0517211 A1 | 12/1992 |
| EP | 0576941 A1 | 1/1994 |
| EP | 206802407 A2 | 5/2008 |
| EP | 2006802406 A2 | 7/2008 |
| GB | 2095994 A | 10/1982 |
| JP | 2239980 A | 9/1990 |
| JP | 10152441 A | 6/1998 |
| JP | 10507762 T | 7/1998 |
| JP | 2001513080 T | 8/2001 |
| JP | 2001524109 T | 11/2001 |
| JP | 2002506418 T | 2/2002 |
| WO | WO-8807378 A1 | 10/1988 |
| WO | WO-95/28838 A1 | 11/1995 |
| WO | WO-9630036 A1 | 10/1996 |
| WO | WO-9747470 A2 | 12/1997 |
| WO | WO-9929685 A1 | 6/1999 |
| WO | WO-0006184 A1 | 2/2000 |
| WO | WO-0006534 A1 | 2/2000 |
| WO | WO-0007979 A2 | 2/2000 |
| WO | WO-0009390 A1 | 2/2000 |
| WO | WO-1148589 A1 | 8/2000 |

OTHER PUBLICATIONS

Brown et al., . Med. Chem. 27:79-81 (1984).
Chem Abs 184360-83-342 (1975) "Solubility and disassociation constants of some alicyclic acids".
Chem Abs 70204-54-5 (Apr. 1991).
Chem Abs 73548-12-6 (Apr. 1991).
Chemical Abstract, vol. 99(23) Abst. No. 191473h (1993).
Gurrier and Siracusa, "Thermal Condensation of Some alpha-aminoacids with Phatalic Acid" Thermochimica Acta, 7 (1973) 231-239.
Ho Koc-Kan; et al. "A Practical Synthesis of ?-aminoalkanoic acid derivatives form Cycloalkanones" Synthetic Communication. vol. 26, No. 14:2641-2649 (1996).
Johansen, Marianne, et al. "The Kinetics of decomp. Of various N-Mannichi bases of salicylamide" Int. J. Pharm. 1980. 7(2); 119-27 (1980).
Leone-Bay, A. "4-[4-(2-Hydroxybenzol) amino]phenyl]-butyric Acids as Novel Oral Delivery Agent for Recombinant Human Growth Hormone": Journal of Medicinal Chemistry vol. 39, No. 18 pp. 2571-2578 (1996).
Leone-Bay, A. "Acylated non-alpha-amino acids as novel agents for the oral delivery of heparing sodium, USP" Journal of Controlled Release 50: 41-49 (1998).
Leone-Bay, A. "N-Acylatated alpha-amino acids as novel oral delivery agents for proteins" ;Journal of Medicinal Chemistry vol. 38, 4263-4269 (1995).
Leone-Bay, A. "N-Acylatated alpha-amino acids as novel oral delivery agents for proteins" ;Journal of Medicinal Chemistry vol. 38, 4257-4262 (1995).
Leone-Bay, A. et al., "The evolution of an oral heparin dosing solution" Drugs of the Future vol. 22 (8) 885-891 (1997).
Leone-Bay, Andrea. et al. 1998. Synthesis and Evaluation of Compounds that Facilitate the Gastrointestinal Absorption of Heparin, J. Med. Chem., vol. 41, pp. 1163-1171.
Picciola G, "Sintesi Di Acidi Chiazolinioici E. Benzossazinonici E Studio Delle Loro Proprieta Antiniammatore" IT, Societa Chimica Italiana Pavia vol. 31, No. 9 pp. 655-664 and English Translation, 1976.
Riviera, Theresa M. et al. "Oral Delivery of Heparin in Combination with Sodium N-[8-2-hydroxybenzoyl)amino]caprylate: Pharmacological Considerations" Pharmaceutical Research vol. 14(12) 1830-1834 (1979).

DISODIUM SALTS, MONOHYDRATES, AND ETHANOL SOLVATES FOR DELIVERING ACTIVE AGENTS

This application is a continuation of U.S. Ser. No. 13/053,641, filed Mar. 22, 2011, now U.S. Pat. No. 8,207,227, which is a continuation of U.S. Ser. No. 12/642,508, filed Dec. 18, 2009, now U.S. Pat. No. 8,003,697, which is a continuation of U.S. Ser. No. 12/111,750, filed Apr. 29, 2008, now U.S. Pat. No. 7,659,311, which is a continuation of U.S. Ser. No. 10/615,213, filed Jul. 7, 2003, now U.S. Pat. No. 7,384,982, which is a continuation of U.S. Ser. No. 09/962,794, filed Sep. 24, 2001, now abandoned, which is a continuation of International Patent Application No. PCT/US00/09390, filed Apr. 5, 2000, which claims the benefit of U.S. patent application Ser. No. 60/127,754, filed Apr. 5, 1999; U.S. patent application Ser. No. 60/186,143, filed Mar. 1, 2000; U.S. patent application Ser. No. 60/186,142, filed Mar. 1, 2000; and U.S. patent application Ser. No. 60/191,286, filed Mar. 21, 2000, each of which is incorporated by reference.

FIELD OF THE INVENTION

The present invention relates to a disodium salt of a delivery agent, such as N-(5-chlorosalicyloyl)-8-aminocaprylic acid, N-(10-[2-hydroxybenzoyl]amino)decanoic acid, or N-(8-[2-hydroxybenzoyl]amino)caprylic acid, an ethanol solvate of the disodium salt, and a monohydrate of the disodium salt for delivering active agents and methods of preparing the same.

BACKGROUND OF THE INVENTION

U.S. Pat. Nos. 5,773,647 and 5,866,536 disclose compositions for the oral delivery of active agents, such as heparin and calcitonin, with modified amino acids, such as N-(5-chlorosalicyloyl)-8-aminocaprylic acid (5-CNAC), N-(10-[2-hydroxybenzoyl]amino)decanoic acid (SNAD), and N-(8-[2-hydroxybenzoyl]amino)caprylic acid (SNAC). Many current commercial formulations containing an active agent, such as heparin and calcitonin, are delivered by routes other than the oral route. Formulations delivered orally are typically easier to administer than by other routes and improve patient compliance.

There is a need for improved pharmaceutical formulations for orally administering active agents, such as heparin and calcitonin.

SUMMARY OF THE INVENTION

The inventors have discovered that the disodium salt of certain delivery agents has surprisingly greater efficacy for delivering active agents than the corresponding monosodium salt. Furthermore, the inventors have discovered that the disodium salts of these delivery agents form solvates with ethanol and hydrates with water. The delivery agents have the formula

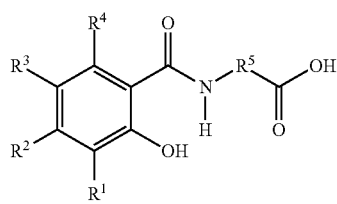

wherein
$R^1$, $R^2$, $R^3$, and $R^4$ are independently hydrogen, —OH, —$NR^6R^7$, halogen, $C_1$-$C_4$ alkyl, or $C_1$-$C_4$ alkoxy;
$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and
$R^6$ and $R^7$ are independently hydrogen, oxygen, or $C_1$-$C_4$ alkyl. The hydrates and solvates of the present invention also have surprisingly greater efficacy for delivering active agents, such as heparin and calcitonin, than their corresponding monosodium salts and free acids.

The present invention provides an alcohol solvate, such as methanol, ethanol, propanol, propylene glycol, and other hydroxylic solvates, of a disodium salt of a delivery agent of the formula above. According to one preferred embodiment, the alcohol solvate is ethanol solvate. The invention also provides a hydrate, such as a monohydrate, of a disodium salt of a delivery agent of the formula above. Preferred delivery agents include, but are not limited to, N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC), 8-(N-2-hydroxy-4-methoxybenzoyl)aminocaprylic acid (as shown as compound 67 in U.S. Pat. No. 5,773,647), and N-(9-(2-hydroxybenzoyl)aminononanic acid (or 9-salicyloylaminononanoic acid) (as shown as compound 35 in U.S. Pat. No. 5,773,647).

The present invention also provides a method of preparing the disodium salt of the present invention by drying the ethanol solvate of the present invention. According to a preferred embodiment, the ethanol solvate is prepared by the method described below.

Another embodiment of the invention is a method of preparing the ethanol solvate of the present invention. The method comprises dissolving a delivery agent of the formula above in ethanol to form a delivery agent/ethanol solution; (b) reacting the delivery agent/ethanol solution with a molar excess of a sodium containing salt to form the ethanol solvate.

Yet another embodiment of the invention is a method of preparing the hydrate of the present invention. The method comprises (a) obtaining an ethanol solvate of the disodium salt of the delivery agent; (b) drying the solvate to form an anhydrous disodium salt; and (c) hydrating the anhydrous disodium salt to form the hydrate.

Yet another embodiment of the present invention is a composition comprising a disodium salt of the delivery agent.

Yet another embodiment of the invention is a composition comprising at least one disodium salt, ethanol solvate, or hydrate of the present invention and at least one active agent. Preferred active agents include, but are not limited to, heparin and calcitonin. The composition may be formulated into a dosage unit form, such as an oral dosage unit form.

Yet another embodiment of the present invention is a method for administering an active agent to an animal in need thereof comprising administering to the animal the composition of the present invention.

DETAILED DESCRIPTION OF THE INVENTION

The term "substituted" as used herein includes, but is not limited to, substitution with any one or any combination of the following substituents: halogens, hydroxide, $C_1$-$C_4$ alkyl, and $C_1$-$C_4$ alkoxy.

The terms "alkyl", "alkoxy", "alkylene", "alkenylene", "alkyl(arylene)", and "aryl(alkylene)" include, but are not limited to, linear and branched alkyl, alkoxy, alkylene, alkenylene, alkyl(arylene), and aryl(alkylene) groups, respectively.

Disodium Salt

The disodium salt may be prepared from the ethanol solvate by evaporating or drying the ethanol by methods known in the art to form the anhydrous disodium salt. Generally, drying is performed at a temperature of from about 80 to about 120, preferably from about 85 to about 90, and most preferably at about 85° C. Typically, the drying step is performed at a pressure of 26" Hg or greater. The anhydrous disodium salt generally contains less than about 5% by weight of ethanol and preferably less than about 2% by weight of ethanol, based upon 100% total weight of anhydrous disodium salt.

The disodium salt of the delivery agent may also be prepared by making a slurry of the delivery agent in water and adding two molar equivalents of aqueous sodium hydroxide, sodium alkoxide, or the like. Suitable sodium alkoxides include, but are not limited to, sodium methoxide, sodium ethoxide, and combinations thereof.

Yet another method of preparing the disodium salt is by reacting the delivery agent with one molar equivalent of sodium hydroxide to form a monosodium salt of the delivery agent and then adding an additional one molar equivalent of sodium hydroxide to yield the disodium salt.

The disodium salt can be isolated as a solid by concentrating the solution containing the disodium salt to a thick paste by vacuum distillation. This paste may be dried in a vacuum oven to obtain the disodium salt of the delivery agent as a solid. The solid can also be isolated by spray drying an aqueous solution of the disodium salt.

The delivery agent may be prepared by methods known in the art, such as those described in U.S. Pat. Nos. 5,773,647 and 5,866,536, respectively.

Another aspect of the invention is a composition comprising at least about 20% by weight and preferably at least about 60% by weight of the disodium salt of the delivery agent, based upon 100% total weight of the delivery agent and salts thereof in the composition. According to one embodiment, the composition comprises at least about 10, 30, 40, 50, 70, or 80% by weight of the disodium salt of the delivery agent, based upon 100% total weight of the delivery agent and salts thereof in the composition. More preferably, the composition comprises at least about 90% by weight of the disodium salt of the delivery agent, based upon 100% total weight of the delivery agent and salts thereof in the composition.

Most preferably, the composition comprises substantially pure disodium salt of the delivery agent. The term "substantially pure" as used herein means that less than about 4% and preferably less than about 2% by weight of the delivery agent in the composition is not a disodium salt, based upon 100% total weight of the delivery agent and salts thereof in the composition.

Ethanol Solvate

The term "ethanol solvate" as used herein includes, but is not limited to, a molecular or ionic complex of molecules or ions of ethanol solvent with molecules or ions of the disodium salt of the delivery agent. Typically, the ethanol solvate contains about one ethanol molecule or ion for every molecule of disodium salt of the delivery agent.

The ethanol solvate of the disodium salt of the delivery agent may be prepared as follows. The delivery agent is dissolved in ethanol. Typically, each gram of delivery agent is dissolved in from about 1 to about 50 mL of ethanol and preferably from about 2 to about 10 mL of ethanol. The delivery agent/ethanol solution is then reacted with a molar excess of a sodium containing salt, such as a monosodium containing salt, relative to the delivery agent, i.e., for every mole of delivery agent there is more than one mole of sodium cations. This reaction yields the ethanol solvate. Suitable monosodium containing salts include, but are not limited to, sodium hydroxide; sodium alkoxides, such as sodium methoxide and sodium ethoxide; and any combination of any of the foregoing. Preferably, at least about two molar equivalents of the monosodium containing salt are added to the ethanol solution, i.e., for every mole of delivery agent there is at least about two moles of sodium cations. Generally, the reaction is performed at a temperature at or below the reflux temperature of the mixture, such as at ambient temperature.

The ethanol solvate may then be recovered by methods known in the art. For example, the slurry resulting from the addition of sodium hydroxide to the delivery agent/ethanol solution may be concentrated by atmospheric distillation. The concentrated slurry may then be cooled and the solid product recovered by filtration. The filter cake, i.e., the filtrate, may be vacuum dried to obtain the ethanol solvate.

Hydrate

The term "hydrate" as used herein includes, but is not limited to, (i) a substance containing water combined in the molecular form and (ii) a crystalline substance containing one or more molecules of water of crystallization or a crystalline material containing free water. Compositions containing the hydrate of the disodium salt preferably contain at least about 80%, more preferably at least about 90%, and most preferably about 95% by weight of the monohydrate of the disodium salt, based upon 100% total weight of hydrate of disodium salt in the composition. According to a preferred embodiment, the composition contains at least about 98% by weight of the monohydrate of the disodium salt, based upon 100% total weight of hydrate of disodium salt in the composition.

The hydrate may be prepared by drying the ethanol solvate to form an anhydrous disodium salt as described above and hydrating the anhydrous disodium salt. Preferably, the monohydrate of the disodium salt is formed. Since the anhydrous disodium salt is very hygroscopic, the hydrate forms upon exposure to atmospheric moisture. Generally, the hydrating step is performed at from about ambient temperature to about 50° C. and in an environment having at least about 50% relative humidity. Preferably, the hydrating step is performed at from about ambient temperature to about 30° C. For example, the hydrating step may be performed at 40° C. and 75% relative humidity. Alternatively, the anhydrous disodium salt may be hydrated with steam.

According to one preferred embodiment, the drying and hydrating steps are performed in an oven. Preferably, the material is not exposed to the atmosphere until both steps are complete.

Disodium Salt, Ethanol Solvate, and Hydrate Compositions and Dosage Unit Forms The invention also provides a composition, such as a pharmaceutical composition, comprising at least one of a disodium salt, ethanol solvate, or hydrate of the present invention and at least one active agent. The composition of the present invention typically contains a delivery effective amount of one or more disodium salts, ethanol solvates, and/or hydrates of the present invention, i.e., an amount of the disodium salt, ethanol solvate, and/or hydrate sufficient to deliver the active agent for the desired effect.

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including $\alpha$, $\beta$, and $\gamma$-interferon; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine, and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof. Preferred active agents include, but are not limited to, heparin and calcitonin.

The amount of active agent in the composition is an amount effective to accomplish the purpose intended. The amount in the composition is typically a pharmacologically, biologically, therapeutically, or chemically effective amount. However, the amount can be less than that amount when a plurality of the compositions are to be administered, i.e., the total effective amount can be administered in cumulative units. The amount of active agent can also be more than a pharmacologically, biologically, therapeutically, or chemically effective amount when the composition provides sustained release of the active agent. Such a composition typically has a sustained release coating which causes the composition to release a pharmacologically, biologically, therapeutically, or chemically effective amount of the active agent over a prolonged period of time.

The total amount of active agent to be used can be determined by methods known to those skilled in the art. However, because the compositions may deliver the active agent more efficiently than prior compositions, lesser amounts of the active agent than those used in prior dosage unit forms or delivery systems can be administered to the subject, while still achieving the same blood levels and/or therapeutic effects.

According to one preferred embodiment, the composition comprises a disodium salt of a delivery agent and calcitonin. Preferably, the delivery agent is 5-CNAC. Generally, the weight ratio of calcitonin to disodium salt of 5-CNAC varies depending on the animal to which the composition is to be administered. For example, for a composition which is to be administered to humans the weight ratio may range from about 1:300 to about 1:700 and is preferably about 1:500. For primates, the weight ratio generally ranges from about 1:100 to about 1:500.

The composition of the present invention may be in liquid or solid form. Preferably, compositions containing the disodium salt and/or hydrate of the present invention are in solid form. The composition may further comprise additives including, but not limited to, a pH adjuster, a preservative, a flavorant, a taste-masking agent, a fragrance, a humectant, a tonicifier, a colorant, a surfactant, a plasticizer, a lubricant, a dosing vehicle, a solubilizer, an excipient, a diluent, a disintegrant, or any combination of any of the foregoing. Suitable dosing vehicles include, but are not limited to, water, phosphate buffer, 1,2-propane diol, ethanol, olive oil, 25% aqueous propylene glycol, and any combination of any of the foregoing. Other additives include phosphate buffer salts, citric acid, glycols, and other dispersing agents. Stabilizing additives may be incorporated into the solution, preferably at a concentration ranging between about 0.1 and 20% (w/v).

The composition may also include one or more enzyme inhibitors, such as actinonin or epiactinonin and derivatives thereof. Other enzyme inhibitors include, but are not limited to, aprotinin (Trasylol) and Bowman-Birk inhibitor.

The composition of the present invention may be prepared by dry mixing or mixing in solution the disodium salt, hydrate, and/or ethanol solvate, active agent, and, optionally, additives. The mixture may be gently heated and/or inverted to aid in dispersing the components in solution.

The composition of the present invention may be formulated into a dosage unit form and in particular an oral dosage unit form, including, but not limited to, capsules, tablets, and particles, such as powders and sachets, by methods known in the art.

According to one preferred embodiment, the dosage unit form is a solid dosage unit form comprising a lyophilized mixture of at least one of a disodium salt, ethanol solvate, or hydrate of the present invention and at least one active agent.

The term "lyophilized mixture" includes, but is not limited to, mixtures prepared in dry form by rapid freezing and dehydration. Typically dehydration is performed while the mixture is frozen and under a vacuum. Lyophilized mixtures generally are substantially free of water and preferably contain less than 4% by weight of water, based upon 100% total weight of the mixture.

Such a solid dosage unit form may be prepared by (a) obtaining a solution comprising one or more delivery agents and one or more active agents, (b) lyophilizing the solution to obtain a lyophilized mixture, and (c) preparing a solid dosage unit form with the lyophilized mixture.

The delivery agent and active agent may be mixed in solution to form the solution in step (a). The solution may be lyophilized by any method known in the art. The lyophilized mixture may be incorporated into a dosage unit form by any method known in the art.

The composition and the dosage unit form of the present invention may be administered to deliver an active agent to any animal in need thereof including, but not limited to, birds, such as chickens; mammals, such as rodents, cows, pigs, dogs, cats, primates, and particularly humans; and insects. The composition and dosage unit form may be administered by the oral, intranasal, sublingual, intraduodenal, subcutaneous, buccal, intracolonic, rectal, vaginal, mucosal, pulmonary, transdermal, intradermal, parenteral, intravenous, intramuscular or ocular route. Preferably, the composition and dosage unit form are administered orally.

The following examples are intended to describe the present invention without limitation.

Example 1

Preparation of
N-(5-chlorosalicyloyl)-8-aminocaprylic acid
(5-CNAC)

To a clean, dry, 200 gallon glass-lined reactor, 178 L of dry acetonitrile was added. The agitator was set to 100-125 rpm and the reactor contents were cooled to about 9° C. 74 kg of 5-chloro salicylamide, available from Polycarbon Industries of Leominster, Mass., was charged to the reactor and the charging port was closed. 47 L of dry pyridine was charged to the reactor. The resulting slurry was cooled to about 9° C. Cooling was applied to the reactor condenser and valve overheads were set for total reflux. Over 2 hours, 49.7 kg of ethylchloroformate was charged to the 200 gallon reactor while maintaining the batch temperature at about 14° C. Ethylchloroformate can contain 0.1% phosgene and is extremely reactive with water. The reaction is highly exothermic and requires the use of a process chiller to moderate reaction temperature.

The reactor contents were agitated for about 30 minutes at 10-14° C., once the ethylchloroformate addition was complete. The reactor contents were then heated to about 85° C. over about 25 minutes, collecting all distillate into a receiver. The reactor contents were held at 85-94° C. for approximately 6 hours, collecting all distilled material into a receiver. The reaction mixture was sampled and the conversion (>90%) monitored by HPLC. The conversion was found to be 99.9% after 6 hours. The reactor contents were cooled to about 19° C. over a one-hour period. 134 L of deionized water was charged to the reactor. A precipitate formed immediately. The reactor contents were cooled to about 5° C. and agitated for about 10.5 hours. The product continued to crystallize out of solution. The reactor slurry was centrifuged. 55 L of deionized water was charged to the 200-gallon, glass-lined reactor and the centrifuge wet cake was washed. The intermediate was dried under full vacuum (28" Hg) at about 58° C. for about 19.5 hours. The yield was 82.6 kg 6-chloro-2H-1,3-benzoxazine-2,4(3H)-dione. This intermediate was packaged and stored so that it was not exposed to water.

In the following preparation, absolutely no water can be tolerated in the steps up to the point where distilled water is added. 222 L of dry dimethylacetamide was charged to a dry 200 gallon glass-lined reactor. The reactor agitator was set to 100-125 rpm. Cooling was applied to the condenser and valve reactor overheads were set for distillation. 41.6 kg of dry anhydrous sodium carbonate was charged to the reactor and the reactor charging port was closed. Caution was used due to some off-gassing and a slight exothermic reaction. 77.5 kg of dry 6-chloro-2H-1,3-benzoxazine-2,4(3H)-dione was charged to the reactor. Quickly, 88 kg of dry ethyl-8-bromooctanoate was charged to the reactor. The reaction was evacuated to 22-24 inches of vacuum and the reactor temperature was raised to 65-75° C. The reactor temperature was maintained and the contents were watched for foaming. The reactor mixture was sampled and monitored for conversion by monitoring the disappearance of the bromo ester in the reaction mixture by gas chromatography. The reaction was complete (0.6% bromo ester was found) after about 7 hours. The vacuum was broken and the reactor contents were cooled to 45-50° C. The contents were centrifuged and the filtrate sent into a second 200 gallon glass-lined reactor. 119 L of ethanol (200 proof denatured with 0.5% toluene) was charged to the first 200 gallon reactor, warmed to about 45° C. The filter cake was washed with warm ethanol and the wash was charged to the reaction mixture in the second 200 gallon reactor.

The agitator was started on the second 200 gallon reactor. The reactor contents were cooled to about 29° C. 120 L distilled water was slowly charged to the second reactor, with the water falling directly into the batch. The reactor contents were cooled to about 8° C. The intermediate came out of solution and was held for about 9.5 hours. The resultant slurry was centrifuged. 70 L ethanol was charged to the reactor, cooled to about 8° C., and the centrifuge cake was washed. The wet cake was unloaded into double polyethylene bags placed inside a paper lined drum. The yield was 123.5 kg of ethyl 8-(6-chloro-2H-1,3-benzoxazine-2,4(3H)-dionyl)octanoate.

400 L purified water, USP and 45.4 kg sodium hydroxide pellets were charged to a 200 gallon glass-lined reactor and the agitator was set to 100-125 rpm. 123.5 kg of the ethyl 8-(6-chloro-2H-1,3-benzoxazine-2,4(3H)-dionyl)octanoate wet cake was charged to the reactor. The charging port was closed. Cooling water was applied to the condenser and the valve reactor overheads were set for atmospheric distillation. The reactor contents were heated to about 98° C. and the conversion was monitored by HLPC. Initially (approximately 40 minutes) the reactor refluxed at about 68° C., however, as the ethanol was removed (over about 3 hours) by distillation the reactor temperature rose to about 98° C. The starting material disappeared, as determined by HPLC, at approximately 4 hours. The reactor contents were cooled to about 27° C. 150 L purified water, USP was charged to an adjacent 200 gallon glass-lined reactor and the agitator was set to 100-125 rpm. 104 L concentrated (12M) hydrochloric acid was charged to the reactor and cooled to about 24° C. The saponified reaction mixture was slowly charged (over about 5 hours) to the 200 gallon glass-lined reactor. The material (45 L and 45 L) was split into 2 reactors (200 gallons each) because of carbon dioxide evolution. The product precipitated out of solution. The reaction mixture was adjusted to pH 2.0-4.0 with a 50% sodium hydroxide solution (2 L water, 2 kg sodium hydroxide). The reactor contents were cooled to about 9-15° C. The intermediate crystallized out of solution over approximately 9 hours. The reactor slurry was centrifuged to isolate the intermediate. 50 L purified water, USP was charged to a 200 gallon glass-lined reactor and this rinse was used to wash the centrifuge wet cake. The wet cake was unloaded into double polyethylene bags placed inside a plastic drum. The N-(5-chlorosalicyloyl)-8-aminocaprylic acid was dried under vacuum (27" Hg) at about 68° C. for about 38 hours. The dry cake was unloaded into double polyethylene bags placed inside a 55-gallon, steel unlined, open-head drums with a desiccant bag placed on top. The dried isolated yield was 81 kg of N-(5-chlorosalicyloyl)-8-aminocaprylic acid.

Example 2

Preparation of Disodium N-(5-chlorosalicyloyl)-8-aminocaprylate

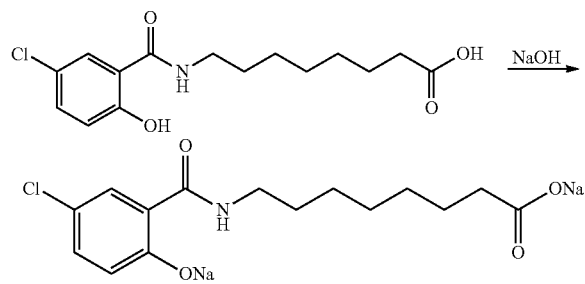

A 22 L, Pyrex glass, five-neck, round bottom flask was equipped with an overhead stirrer, thermocouple temperature read out, and heating mantle. The flask was charged with 2602.3 g of N-(5-chlorosalicyloyl)-8-aminocaprylic acid and 4000 mL water. To this stirred slurry was added a solution of 660 g of sodium hydroxide dissolved in 2000 mL water. The mixture was heated to about 55° C. and most of the solids dissolved. The slightly hazy solution was hot filtered through Whatman #1 filter paper to remove the insoluble particulates. The filtrate was transferred to the pot flask of a large laboratory rotary evaporator. The rotary evaporator was operated with a bath temperature of about 60° C. and a pressure of 60 mmHg. Water was removed from the disodium salt solution until a solid mass was obtained in the rotary evaporator pot flask. The vacuum was released and pot flask removed from the rotary evaporator. The solids were scraped from the pot flask into trays. These trays were then placed in a vacuum oven and the solids dried at about 60° C. and full vacuum for about 48 hours. The dried solids were run through a laboratory mill until all the solids passed through a 35 mesh screen. The milled and sieved disodium N-(5-chlorosalicyloyl)-8-aminooctanate was put into trays and placed back into the drying oven. Drying was continued at about 45° C. and full vacuum to obtain 2957.1 g of the desired product as a dry powder.

Titration of the product with hydrochloric acid gave two inflection points consuming approximately 2 molar equivalents of hydrochloric acid. CHN analysis: theoretical (correcting 4.9 wt % water) C, 47.89%; H, 5.37%; N, 3.72%; Na, 12.22%; actual C, 47.69%; H, 5.23%; N, 3.45%; Na, 11.79%.

Example 3

Preparation of Monosodium N-(5-chlorosalicyloyl)-8-aminocaprylate

A 22 L, Pyrex glass, five-neck, round bottom flask was equipped with an overhead stirrer, thermocouple temperature read out, and heating mantle. The flask was charged with 2099.7 g of N-(5-chlorosalicyloyl)-8-aminooctanoic acid and 6000 mL water and stirred. To this slurry was added a solution of 265 g of sodium hydroxide dissolved in 2000 mL water. The mixture was heated to about 80° C. causing most of the solids to dissolve. The undissolved material was allowed to settle to the bottom of the flask and the supernate decanted. The resulting mixture was transferred to the pot flask of a large laboratory rotary evaporator. The rotary evaporator was operated with a bath temperature of about 60° C. and a pressure of about 70 mmHg. Water was removed from the disodium salt mixture until a solid mass was obtained in the rotary evaporator pot flask. The vacuum was released and pot flask removed from the rotary evaporator. The solids were scraped from the pot flask into trays. These trays were then placed in a vacuum oven and the solids dried at about 60° C. and full vacuum for about 48 hours. The dried solids were run through a laboratory mill until all the solids passed through a 35 mesh screen. The milled and seived disodium N-(5-chlorosalicyloyl)-8-aminooctanate was put into trays and placed back into the drying oven. Drying was continued at full vacuum to yield 2161.7 g of the desired product as a dry powder.

Titration of the product with hydrochloric acid gave a single inflection point consuming approximately 1 molar equivalent of hydrochloric acid. CHN analysis: theoretical (correcting 1.14 wt % water) C, 53.05%; H, 5.77%; N, 4.12%; Na, 6.77%; actual C, 52.57%; H, 5.56%; N, 4.06%; Na, 6.50%.

Example 4

Disodium and monosodium salts of 5-CNAC were dosed to Rhesus monkeys as follows. Six monkeys in one group were each dosed with one capsule containing the disodium salt, while six monkeys in a second group were each dosed with one capsule containing the monosodium salt. Each capsule was prepared by hand-packing 400 mg 5-CNAC (mono- or di-sodium salt) and 800 μg salmon calcitonin (sCT) into a hard gelatin capsule.

The Rhesus monkeys were fasted overnight prior to dosing and were restrained in chairs, fully conscious, for the duration of the study period. The capsules were administered via a gavage tube followed by 10 ml water.

Blood samples were collected at 15, 30, and 45 minutes and at 1, 1.5, 2, 3, 4, 5, and 6 hours after administration. Plasma concentration sCT was determined by radio-immunoassay. The results from the six monkeys in each dosing group were averaged for each time point and plotted. The maximum mean plasma calcitonin concentration and the area under the curve (AUC) are reported below in Table 1.

TABLE 1

| Delivery Agent | Delivery Agent Dose (mg) | sCT Dose (mg) | Mean Peak Plasma Calcitonin Concentration (pg/ml ± Standard Deviation) (Standard Error) | AUC |
|---|---|---|---|---|
| Disodium salt of 5-CNAC | 400 | 800 | 424 ± 230 (94) | 883 |
| Monosodium salt of 5-CNAC | 400 | 800 | 93.2 ± 133 (54) | 161 |

Example 5

N-(10-[2-hydroxybenzoyl]amino)decanoic acid was prepared by the procedure described in Example 1 using the appropriate starting materials.

Example 6

Preparation of Disodium N-salicyloyl-10-aminodecanoate Ethanol Solvate

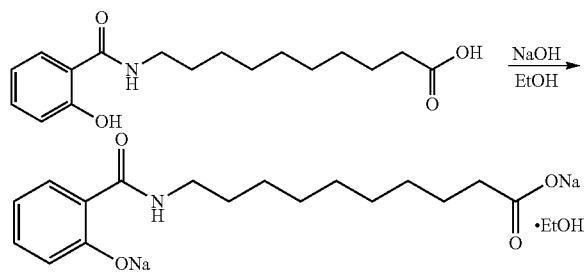

A 1 L Pyrex glass, four-neck, round bottom flask was equipped with an overhead stirrer, reflux condenser, thermocouple temperature read out, and heating mantle. The flask was purged with dry nitrogen and the following reaction conducted under an atmosphere of dry nitrogen. The flask was charged with 100 g of N-salicyloyl-10-aminodecanoic acid and 500 mL absolute ethanol. The slurry was heated to about 40° C. with stirring and all of the solids were dissolved. An addition funnel was attached to the reactor and charged with 232.5 g of 11.2 wt % sodium hydroxide dissolved in absolute ethanol. The sodium hydroxide solution was added to the stirred reaction mixture over a fifteen minute period. The reflux condenser was removed from the reactor and replaced with a distillation head and receiver. The reaction mixture was distilled at atmospheric pressure until about 395 g of distillate was collected. The reaction mixture had become a thick slurry during this distillation. The mixture was allowed to cool to room temperature. The thick mixture was transferred to a sintered glass funnel and the solids recovered by vacuum filtration. The ethanol wet cake was placed in a 45° C. vacuum oven and dried to constant weight at full vacuum. The dried material had a weight of about 124.6 g.

Titration of the product with hydrochloric acid gave two inflection points consuming approximately 2 molar equivalents of hydrochloric acid. CHN analysis: theoretical (correcting 0.47 wt % water) C, 57.15%; H, 7.37%; N, 3.51%; Na, 11.51%; actual C, 57.30%; H, 7.32%; N, 3.47%; Na, 11.20%.

Example 7

Preparation of Disodium N-(5-chlorosalicyloyl)-8-aminocaprylate Ethanol Solvate

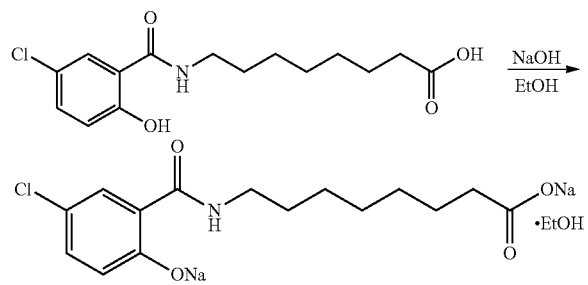

A 12 L, Pyrex glass, four-neck, round bottom flask was equipped with an overhead stirrer, thermocouple temperature read out, reflux condenser, and heating mantle. The flask was purged with dry nitrogen and the following reaction was conducted under an atmosphere of dry nitrogen. The flask was charged with 1000 g of N-(5-chloro-salicyloyl)-8-aminooctanic acid and 3000 mL of absolute ethanol. This slurry was heated to 55° C. with stirring to obtain a slightly hazy solution. The reactor was then charged with 2276 g of 11.2 wt % sodium hydroxide dissolved in absolute ethanol as rapidly as possible. There was a slight exothermic reaction causing the temperature in the reactor to rise to about 64° C. and a precipitate began to form. The reflux condenser was removed and the reactor set for distillation. The reaction mixture was distilled over the next three hours to obtain about 2566 g of distillate. The pot slurry was allowed to cool slowly to room temperature. The product solids in the slurry were recovered by vacuum filtration through a sintered glass funnel to obtain 1390 g of ethanol wet cake. The wet cake was transferred to glass trays and placed in a vacuum oven. The cake was dried to constant weight at about 45° C. and full vacuum. The dry product had a weight of about 1094.7 g.

Titration of the product with hydrochloric acid gave two inflection points consuming approximately 2 molar equivalents of hydrochloric acid. CHN analysis: theoretical (correcting 0 wt % water) C, 50.56%; H, 5.99%; N, 3.47%; Na, 11.39%; actual C, 50.24%; H, 5.74%; N, 3.50% (Na was not measured).

Example 8

Preparation of Monosodium N-(10-[2-hydroxybenzoyl]amino)decanoate

A 22 L, Pyrex glass, five-neck, round bottom flask was equipped with an overhead stirrer, thermocouple temperature read out, and heating mantle. The flask was charged with 801.8 g of N-(10-[2-hydroxybenzoyl]amino)decanoic acid and 6000 mL water and stirred. To this slurry was added a solution of 104 g of sodium hydroxide dissolved in 3000 mL water. The mixture was heated to about 63° C. causing most of the solids to dissolve. The resulting slightly hazy mixture was transferred to a pot flask of a large laboratory rotary evaporator. Water was removed from the monosodium salt solution until a solid mass was obtained in the rotary evaporator pot flask. The vacuum was released and pot flask removed from the rotary evaporator. The solids were scraped from the pot flask into trays. These trays were then placed in a vacuum oven and the solids dried at about 80° C. and full vacuum for about 48 hours. The dried solids were identified as the desired monosodium salt. The weight of the dried material was 822.4 g.

Titration of the product with hydrochloric acid gave one inflection point consuming approximately 1 molar equivalents of hydrochloric acid. CHN analysis: theoretical (correcting 0.549 wt % water) C, 61.65%; H, 7.37%; N, 4.23%; Na, 6.94%; actual C, 61.72%; H, 7.38%; N, 3.93%; Na, 6.61%.

Example 9

Preparation of Disodium N-salicyloyl-10-aminodecanoate Ethanol Solvate/Heparin Capsules Disodium N-salicyloyl-10-aminodecanoate (SNAD) ethanol solvate was screen through a 20 mesh sieve. 7.77 g of the screened disodium SNAD ethanol solvate was weighed out and transferred to a mortar. 1.35 g of heparin sodium, USP (182 units/mg), available from Scientific Protein Laboratories, Inc., of Waunakee, Wis., was weighed out and added to the disodium SNAD ethanol solvate in the mortar. The powders were mixed with the aid of a spatula. The mixed powders were transferred to a 1 pint V-blender shell, available from Patterson-Kelley Co. of East Stroudsburg, Pa., and mixed for about 5 minutes.

Size 0 hard gelatin capsules, available from Torpac Inc. of Fairfield, N.J., were each hand filled with about 297-304 mg of the disodium SNAD ethanol solvate/heparin powder. The mean weight of the powder in each capsule was about 300.4 mg and the mean total weight of the capsules (i.e. the weight of the capsule with the powder) was about 387.25 g. Each capsule contained about 259.01 mg disodium SNAD ethanol solvate and about 45.0 mg of heparin.

Example 10

Preparation of Monosodium SNAD/Heparin Tablets

Monosodium SNAD/heparin tablets were prepared as follows. SNAD was screened through a 35 mesh sieve. 150.3 g of SNAD, 27.33 g of heparin sodium USP (available from Scientific Protein Laboratories, Inc., of Waunakee, Wis.), 112.43 g of Avicel™ PH 101 (available from FMA Corporation of Newark, Del.), 6.0 g of Ac-Di-Sol™ (available from FMA Corporation), and 2.265 g of talc (Spectrum Chemicals of New Brunswick, N.J.) were weighed out and transferred to a 2 quart V-blender shell, available from Patterson Kelley of East Stroudsburg, Pa., and blended for about 5 minutes. The resulting blend was compressed into slugs using an EK-O tablet press, available from Korsch America Inc, of Sumerset, N.J. The resulting slugs were crushed and sieved through a 20 mesh sieve to produce granules. 3.94 g of talc and 5.25 g of Ac-Di-Sol were added to the granules and transferred to a 2 quart V-blender shell and mixed for about 5 minutes. 2.72 g of magnesium stearate were added to the granules in the V-blender and mixed for an additional 3 minutes. The resulting formulation was made into tablets using an EK-O tablet press. The mean tablet weight was 320.83 mg.

Example 11

4 cynomolgus macaque monkeys (2 male, 2 female) weighing about 3.0 kg each were dosed with two of the capsules as prepared in Example 9 above. The dose for each monkey was about 150 mg/kg of the disodium SNAD ethanol solvate and about 30 mg/kg of heparin.

The dosing protocol for administering the capsules to each animal was as follows. The animal was deprived food overnight prior to dosing (and 2 hours post dosing). Water was available throughout the dosing period and 400 ml juice was made available to the animal overnight prior to dosing and throughout the dosing period. The animal was restrained in a sling restraint. A capsule was placed into a "pill gun", which is a plastic tool with a cocked plunger and split rubber tip to accommodate a capsule. The pill gun was inserted into the esophagus of the animal. The plunger of the pill gun was pressed to push the capsule out of the rubber tip into the esophagus. The pill gun was then retracted. The animal's mouth was held closed and approximately 5 ml reverse osmosis water was administered into the mouth from the side to induce a swallowing reflex. The throat of the animal was rubbed further to induce the swallowing reflex.

Blood samples (approximately 1.3 ml) were collected from an appropriate vein (femoral, brachial or saphenous) before dosing and 10, 20, 30, 40 and 50 minutes and 1, 1.5, 2, 3, 4 and 6 hours after dosing. Blood samples were collected into a tube with about 0.13 ml of about 0.106 M citrate solution. Blood was added to fill the tube to the 1.3 ml line. The tube was then placed on wet ice pending centrifugation. Blood samples were centrifuged and refrigerated (2-8° C.) for about 15 minutes at 2440 rcf (approximately 3680 rpm). The resultant plasma was divided into 2 aliquots, stored on dry ice or frozen (at approximately −70° C.) until assayed.

Assaying

Plasma heparin concentrations were determined using the anti-Factor Xa assay CHROMOSTRATE™ heparin anti-$X_a$ assay, available from Organon Teknika Corporation of Durham, N.C. Results from the animals were averaged for each time point. The maximum averaged value, which was reached at about 1 hour after administration, was 1.54±0.17 IU/mL.

Comparative Example 11A

The procedure in Example 11 was repeated with tablets of the monosodium salt of SNAD as prepared in Example 10 instead of the capsules of the ethanol solvate of the disodium salt of SNAD. Two tablets were dosed to each of approximately 4.0 kg monkeys. The dosage was approximately 150 mg/kg SNAD (free acid equivalent) and 30 mg/kg heparin. The maximum average-plasma heparin concentration was reached at 2 hours after administration and was 0.23±0.19 IU/mL.

Example 12

Preparation of Mono-Sodium
N-(8-[2-hydroxybenzoyl]amino)caprylate (SNAC)
Salt

The free acid of SNAC (i.e. N-(8-[2-hydroxybenzoyl]amino)caprylic acid) was prepared by the method of Example 1 using the appropriate starting materials.

Into a clean 300 gallon reactor was charged 321 L of ethanol, which was denatured with 0.5% toluene. While stirring, 109 kg (dry) of the free acid of SNAC was added. The reactor was heated to 28° C. and maintained at a temperature above 25° C. A solution of 34 L purified water, USP and 15.78 kg sodium hydroxide was prepared, cooled to 24° C., and added to the stirring reactor over 15 minutes, keeping the reaction temperature at 25-35° C. The mixture was stirred for an additional 15 minutes.

Into an adjacent reactor was charged 321 L of ethanol, which was denatured with 0.5% toluene. The reactor was heated to 28° C. using a circulator. The solution from the first reactor was added to the second reactor over 30 minutes, keeping the temperature above 25° C. The contents were stirred and 418 L of heptane was added. The reaction mixture was cooled to 10° C., centrifuged and then washed with 60 L of heptane. The product was collected and dried in a Stokes oven at 82° C. under 26" Hg vacuum for about 65 hours (over a weekend). 107.5 kg monosodium SNAC (i.e. the monosodium salt of N-(8-[2-hydroxybenzoyl]amino)caprylic acid) was recovered.

Example 13

Preparation of SNAC Di-Sodium Salt

Free acid of SNAC (i.e. N-(8-[2-hydroxybenzoyl]amino)caprylic acid) was prepared as follows. The monosodium SNAC prepared in Example 12 was acidified with 1 equivalent of concentrated hydrochloric acid in water and stirred. The solution was then vacuum filtered and vacuum dried to yield the free acid.

100 g of the free acid of SNAC was weighed into a 2 liter 4-neck round bottomed flask and 500 ml anhydrous ethanol was added. The temperature was set to about 40° C. to allow the solids to go into solution. 255.7 g of 112% (w/w) sodium hydroxide solution in ethanol was added by addition funnel over 15 minutes as the temperature was raised to about 82° C. 383.1 g ethanol was distilled off at a head temperature of about 76-79° C. over about 1.5 hours. The reaction mixture was allowed to cool to room temperature over nitrogen, held for about 2 hours, and vacuum filtered through a coarse funnel to recover the solids. The filter cake was washed with the filtrate, transferred to an evaporating dish, and pulled under full vacuum at room temperature overnight in a dessicator. 90.5 g (68%) ethanol solvate di-sodium salt of SNAC as a pink solid was recovered. Melting point >200° C. (limit of instrument used). HPLC trace showed 100 area %. NMR showed desired product. CHN for $C_{17}H_{25}NO_5Na_2 \cdot 0.1265H_2O$) calculated: C, 54.94; H, 6.85; N, 3.77; Na, 12.37: found: C, 55.04; H, 6.56; N, 3.89; Na, 12.34.

The di-sodium salt, monohydrate of SNAC was made by drying the ethanol solvate made above at 80° C. full vacuum for 22.75 hours and cooling at room temperature open to air to form the monohydrate. The structure of the hydrate was verified by elemental analysis: calculated for $C_{15}H_{19}NO_4Na_2 \cdot 0.127H_2O$: C, 53.01; H, 6.18; N, 4.12; Na, 13.53; found: C, 53.01; H, 6.10; N, 3.88; Na, 13.08; and by $^1$HNMR (300 MHz, DMSO-d6): d 12.35 (1H, s), 7.55 (1H, dd), 6.8 (1H, dt), 6.25 (1H, dd), 6.00 (1H, dt), 3.2 (2H, q), 1.9 (2H, t), 1.45 (4H, bq), 1.25 (6H, bm). Melting point >250° C. (limit of instrument used).

Example 14

Preparation of SNAD Mono-Sodium Salt

The free acid of SNAD may be prepared by the method described in Example 1 using the appropriate starting materials.

206 L ethanol denatured with 0.5% toluene and 33.87 kg SNAD were charged to a reactor, stirred for 1 hour, and sent through a filter press. 1.7 kg Celite (diatomaceous earth), which is available from Celite Corporation of Lompoc, Calif., was added to the reactor. The contents of the reactor were sent through a filter press and the solution was retained in a separate vessel. The reactor was rinsed with 5 gallons of deionized water. The solution was reintroduced to the reactor with a sodium hydroxide (NaOH) solution made from 4.5 kg NaOH in 12 L deionized water. The reactor contents were stirred for 30 minutes and 30 gallons of solvent were removed by vacuum stripping at elevated temperature. The reactor contents were cooled to 60° C. and then poured into two 100 gallon tanks containing 65 gallons heptane each, with rapid stirring. Stirring was continued for 2 hours. The solution was centrifuged, washed with 15 gallons heptane, spun dry, dried in an oven at 45° C. under 26" Hg for 24 hours, and then sent through a Fitzmill grinder (available from the Fitzpatrick Company of Elmhurst, Ill.). 32 kg of the monosodium salt form of SNAD was recovered as a light tan powder (melting point 190-192° C., 99.3% pure by HPLC, molecular weight: 329.37). Titration revealed about 96% mono-sodium and about 4% di-sodium salt form of SNAD.

Example 15

Preparation of SNAD Di-Sodium Salt

The free acid of SNAD (N-(10-[2-hydroxybenzoyl]amino) decanoic acid) was prepared by the method described in Example 1 using the appropriate starting materials.

100 g of the free acid of SNAD was weighed into a 1 liter 4-neck round bottomed flask. 500 ml anhydrous ethanol was charged to the flask. The temperature was set to about 40° C. to allow the solids to go into solution. A light orange solution was obtained. 232.5 g of 11.2 (w/w) sodium hydroxide solution in ethanol was added by addition funnel over 15 minutes as the temperature was raised to about 82° C. 397.8 g ethanol was distilled off at a head temperature of about 75-79° C. over about 3 hours. The reaction mixture was allowed to cool to room temperature overnight under nitrogen. The resulting slurry was vacuum filtered through a coarse funnel to recover the solids and the filter cake was washed with the filtrate. The wet filter cake was transferred to an evaporating dish and placed into a 50° C. oven under full vacuum overnight. 124.55 g (96%) SNAD di-sodium salt, ethanol solvate as a pale pink solid was recovered. Melting point >200° C. (limit of instrument used). HPLC trace showed 100 area %. NMR showed desired product. CHN for $C_{19}H_{29}NO_6Na_2$) calculated: C, 57.42; H, 7.35; N, 3.52; Na, 11.57; found: C, 57.37; H, 7.35; N, 3.41; Na, 11.63.

The di-sodium salt, monohydrate of SNAD was made by drying the ethanol solvate made above at about 80° C. full vacuum for about 19 hours and cooling the solution at room temperature open to air to form the monohydrate. The structure of the hydrate was verified by elemental analysis: calculated for $C_{17}H_{23}NO_4Na_2 \cdot H_2O$: C, 55.28; H, 6.82; N, 3.79; Na, 12.45; found: C, 56.03; H, 6.67; N, 3.67; Na, 12.20; and $^1$H NMR (300 MHz, DMSO-$d_6$): d 12.35 (1H, s), 7.6 (1H, dd), 6.8 (1H, dt), 6.25 (1H, dd), 6.00 (1H, dt), 3.2 (2H, q), 2.0 (2H, t), 1.9 (2H, t), 1.45 (4H, bt), 1.25 (10H, bm). Melting point >250° C. (limit of instrument used).

Example 16

Oral Delivery of Heparin

Oral gavage (PO) dosing solutions containing heparin sodium USP and either the mono-sodium or di-sodium salt form of the delivery agent compound SNAC were prepared in water. The delivery agent compound and heparin (166.9 IU/mg) were mixed by vortex as dry powders. This dry mixture was dissolved in water, vortexed and sonicated at about 37° C. to produce a clear solution. The pH was not adjusted. The final volume was adjusted to about 10.0 ml. The final delivery agent compound dose, heparin dose and dose volume amounts are listed below in Table 2 below.

The typical dosing and sampling protocols were as follows. Male Sprague-Dawley rats weighing between 275-350 g were fasted for 24 hours and were anesthetized with ketamine hydrochloride (about 88 mg/kg) intramuscularly immediately prior to dosing and again as needed to maintain anesthesia. A dosing group of ten rats was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Citrated blood samples were collected by cardiac puncture 0.25, 0.5, 1.0 and 1.5 hours after administration. Heparin absorption was verified by an increase in clotting time as measured by the activated partial thromboplastin time (APTT) according to the method of Henry, J. B., Clinical Diagnosis and Management by Laboratory Methods, Philadelphia, Pa., W.B. Saunders (1979). Previous studies indicated baseline values of about 20 seconds. Results from the animals in each group were averaged for each time point and the maximum APTT value (in seconds) is reported below in Table 2. Heparin absorption was also verified by an increase in plasma heparin measured by the anti-Factor Xa assay CHROMOSTRATE® Heparin anti-$X_a$ assay, available from Organon Teknika Corporation of Durham, N.C. Baseline values are about zero IU/ml. Plasma heparin concentrations from the animals in each group were averaged for each time point and plotted. The peak of these mean plasma heparin concentrations is reported below in Table 2.

TABLE 2

| Compound | Volume Dose (ml/kg) | Compound Dose (mg/kg) | Heparin Dose (mg/kg) | Mean Peak APTT (sec) ± SE | Mean Peak Factor Xa (IU · ml) ± SE |
|---|---|---|---|---|---|
| SNAC-mono | 3 | 300 | 100 | 247 ± 28.5 | 2.597 ± 0.13 |
| SNAC-di | 3 | 300 | 100 | 300 ± 0 | 2.81 ± 0.17 |

Example 17

Oral Delivery of Low Molecular Weight Heparin (LMWH)

Oral dosing (PO) compositions containing low molecular weight heparin (LMWH) and either the mono-sodium or di-sodium salt form of the delivery agent compound SNAD were prepared in water. The delivery agent compound and LMWH (Pamaparin, 91 IU/mg, average molecular weight about 5,000), available from Opocrin of Modena, Italy, were mixed by vortex as dry powders. The dry mixture was dissolved in water, vortexed, and sonicated at about 37° C. to produce a clear solution. The pH was not adjusted. The final volume was adjusted to about 10.0 ml. The final delivery agent compound dose, LMWH dose, and dose volume amounts are listed below in Table 3 below.

The dosing was performed as described in Example 16 above.

Citrated blood samples were collected by cardiac puncture 0.5, 1.0, 2.0, 3.0 and 4.0 hours after administration. Heparin absorption was verified by an increase in plasma heparin measured by the anti-Factor Xa assay CHROMOSTRATE® Heparin anti-$X_a$ assay, available from Organon Teknika Corporation of Durham, N.C. Baseline values were determined earlier and found to be about zero IU/ml. Plasma heparin concentrations from the animals in each group were averaged for each time point and plotted. The peak of these mean plasma heparin concentrations is reported below in Table 3.

TABLE 3

| Compound | Volume Dose (ml/kg) | Compound Dose (mg/kg) | LMWH Dose (mg/kg) | Mean Peak Plasma Heparin Concentration (IU/ml) ± SE |
|---|---|---|---|---|
| SNAD-mono | 3 | 300 | 3000 | 0.88 ± 0.17 |
| SNAD-di | 3 | 300 | 3000 | 1.21 ± 0.15 |

Example 18

Preparation of N-(5-chlorosalicyloyl)-8-aminocaprylic acid (5-CNAC)

5-chlorosalicylamide (280 g, 1.6 mol) and acetonitrile (670 ml) were placed in a 5 liter, 4-neck, round bottomed, flask under a nitrogen atmosphere and stirred. Pyridine (161.3 g, 2.0 mol) was added over a period of 25 minutes to the mixture. The reaction vessel was placed in an ice/water bath and portionwise addition of ethyl chloroformate was started. This addition continued over a period of one hour. When the addition was completed the ice/water bath was removed and the reaction mixture was allowed to come to room temperature. The reaction mixture was allowed to stir for an additional one hour at room temperature before the reaction vessel was reconfigured for distillation at atmospheric pressure. The distillation that followed yielded 257.2 g of distillate at a head temperature of 78° C. 500 ml of deionized water was added to the reaction mixture that remained in the flask and the resulting slurry was vacuum filtered. The filter cake was washed with 200 ml deionized water and was allowed to dry overnight in vacuo at room temperature. 313.6 g (97.3%) of 6-chloro carsalam was isolated after drying. An additional batch was made using this same method, yielding 44.5 g 6-chloro-2H-1,3-benzoxazine-2,4(3H)-dione.

Sodium carbonate (194.0 g, 1.8 mot) was added to a 5 liter, 4-neck, round bottomed, flask containing 6-chloro-2H-1,3-benzoxazine-2,4(3H)-dione (323.1 g, 1.6 mol) and dimethylacetamide (970 ml). Ethyl-8-bromooctanoate (459.0 g, 1.8 mol) was added in one portion to the stirring reaction mixture. The atmospheric pressure in the reaction vessel was reduced to 550 mm Hg and heating of the reaction mixture was started. The reaction temperature was maintained at 70° C. for approximately 5 hours before heating and vacuum were discontinued. The reaction mixture was allowed to cool to room temperature overnight. The reaction mixture was vacuum filtered and the filter cake was washed with ethyl alcohol (525 ml). Deionized water (525 ml) was slowly added to the stirred filtrate and a white solid precipitated. An ice/water bath was placed around the reaction vessel and the slurry was cooled to 5° C. After stirring at this temperature for approximately 15 minutes the solids were recovered by vacuum filtration and the filter cake was washed first with ethanol (300 ml) and then with heptane (400 ml). After drying overnight at room temperature in vacuo, 598.4 g (99.5%) of ethyl 8-(6-chloro-2H-1,3-benzoxazine-2,4(3H)-dionyl)octanoate was obtained. An additional 66.6 g of ethyl 8-(6-chloro-2H-1,3-benzoxazine-2,4(3H)-dionyl)octanoate was made by this same method.

Ethyl 8-(6-chloro-2H-1,3-benzoxazine-2,4(3H)-dionyl) octanoate (641 g, 1.7 mol) and ethyl alcohol (3200 ml) were added to a 22 liter, five neck flask. In a separate 5 liter flask, sodium hydroxide (NaOH) (288.5 g, 7.2 mol) was dissolved in deionized water (3850 ml). This mixture was added to the reaction mixture contained in the 22 liter flask. A temperature increase to 40° C. was noted. Heating of the reaction mixture was started and when the reaction temperature had increased to 50° C. it was noted that all of the solids in the reaction mixture had dissolved. A temperature of 50° C. was maintained in the reaction mixture for a period of 1.5 hours. The reaction flask was then set up for vacuum distillation. 2200 ml of distillate were collected at a vapor temperature of 55° C. (10 mm Hg) before the distillation was discontinued. The reaction flask was then placed in an ice/water bath and concentrated hydrochloric acid (HCl) (752 ml) was added over a period of 45 minutes. During this addition the reaction mixture was noted to have thickened somewhat and an additional 4 liters of deionized water was added to aid the stirring of the reaction mixture. The reaction mixture was then vacuum filtered and the filter cake was washed with 3 liters of deionized water. After drying in vacuo at room temperature 456.7 g (83.5%) of N-(5-chlorosalicyloyl)-8-aminocaprylic acid was isolated.

Example 19

Lyophilization of Salmon Calcitonin (sCT) and the Sodium Salt of 5-CNAC

Preparation of the Sodium Salt of 5-CNAC

The percent purity of 5-CNAC was determined as follows. 0.9964 g of the free acid of 5-CNAC was quantitatively dissolved in 40 ml of methanol. 2 ml of distilled water was added to this solution after the solids were dissolved. The solution was titrated in methanol with 0.33 N sodium hydroxide using a computer controlled burette (Hamilton automatic burette available from Hamilton of Reno, Nev.). A glass electrode (computer controlled Orion model 525A pH meter available from VWR Scientific of South Plainfield, N.J.) was used to monitor the pH of the solution. The solution was stirred with a magnetic stirrer.

The volume of titrant to reach the second pH inflection point was 18.80 ml. The inflection point, determined by interpolation between the two data points where the second derivative of the pH plot changed from positive to negative, occurred at pH 11.3. The purity of the free acid was determined using the following equation:

$$\% \text{ purity} = \frac{100 \times (\text{Volume of Titrant in ml}) \times \text{Normality} \times \text{Molecular Weight}}{1000 \times \text{Equivalents} \times \text{Sample Weight}}$$

where Normality is the normality of sodium hydroxide, Molecular Weight is the molecular weight of 5-CNAC free acid (313.78), Equivalents is the equivalence of free acid (2 in this case, since it is dibasic), and Sample Weight is the weight of the free acid sample being titrated.

The purity was found to be 97.0%.

9.3458 g 5-CNAC powder was weighed out. The amount of 0.33 N sodium hydroxide needed to have a sodium hydroxide to free acid molar ratio of 1.6 was calculated using the following equation:

$$\text{Volume of NaOH (in ml)} = \frac{\text{Free Acid Weight} \times (\% \text{ purity}) \times 1000 \times 1.6}{313.78 \times 100 \times \text{Normality}}$$

where the Free Acid Weight is the weight of free acid in formulated sample, the % purity is the percentage purity of 5-CNAC, Normality is the normality of sodium hydroxide, and the Volume of NaoH is the amount of sodium hydroxide needed.

5-CNAC and 153.3 ml of 0.33 N sodium hydroxide (NaOH) was mixed in a Pyrex bottle. The resulting slurry was warmed in a steam bath to 60-80° C. The warm slurry became a clear solution in about 15 minutes with occasional stirring. The solution was cooled to room temperature. The pH of this solution was 8.1.

Preparation of sCT/Sodium Salt of 5-CNAC Solution

The aqueous solution of 5-CNAC sodium salt was filtered through a sterile, 0.45 micron cellulose acetate, low protein binding membrane on a 150 ml Corning filter (available from VWR Scientific Product, S. Plainfield, N.J.). The pH of the solution was about 8.3.

Dry salmon calcitonin (sCT), stored at −70° C., was brought to room temperature. Next, 18.692 mg of sCT was weighed out and dissolved in 10 ml of 0.1 M mono sodium phosphate buffer solution at a pH of about 5, with gentle mixing.

The sCT solution was added to the 5-CNAC sodium salt solution with gentle mixing, taking precaution to avoid foaming or vortexing.

Lyophilization of sCT/Sodium Salt of 5-CNAC Solution

Shelves of the lyophilizer (Genesis 25 LL-800 from The Virtis Company of Gardiner, N.Y.) were prefrozen to about −45° C.

Approximately 260 ml of sCT/sodium salt of 5-CMAC solution was added to a 30 cm×18 cm stainless steel tray to give a cake thickness of about 0.48 cm. Four clean, dry thermocouple probe tips were inserted into the solution such that the probe tip touched the solution level in the center. The probes were secured with clips to the side of the tray and the trays were loaded on to the precooled shelves.

The gel permeation chromatograph (GPC2) was programmed for the cycle shown in Table 4.

TABLE 4

| Lyophilization Process Cycle | | | |
|---|---|---|---|
| Step | Temperature | Pressure set point (m torr) | Time (minute) |
| 1 | −45° C. | none (Prefreeze) | 120 |
| 2 | −30° C. | 300 | 180 |
| 3 | −20° C. | 200 | 200 |
| 4 | −10° C. | 200 | 360 |
| 5 | −0° C. | 200 | 720 |
| 6 | 10° C. | 100 | 540 |
| 7 | 20° C. | 100 | 360 |
| 8 | 25° C. | 100 | 180 |

During lyophilization the pressure varied from 350 to 45 mtorr. When the lyophilization cycle was completed, the system cycle was terminated and the system vacuum was released. The trays were carefully removed from the shelves and the lyophilized powder was transferred into amber HDPE NALGENE® bottles, available from VWR Scientific.

Using the above cycle for lyophilization, a powder with about 3% moisture content was obtained. The powder was hand packed into hard gelatin capsules (size 0EL/CS), which are available from Capsugel, a division of Warner Lamber Co., of Greenwood, S.C., as needed. The filled capsules and the lyophilized powder were stored in a closed container with desiccant.

Example 20

Preparation of Unlyophilized sCT/Sodium Salt of 5-CNAC

Acetic anhydride (56.81 ml, 61.47 g, 0.6026 mol), 5-chlorosalicylic acid (100.00 g, 0.5794 mol), and xylenes (200 ml) were added to a 500 ml, three-neck flask fitted with a magnetic stir bar, a thermometer, and a Dean-Stark trap with condenser. The flask was heated to reflux, the reaction mixture clearing to a yellow solution around 100° C. Most of the volatile organics (xylenes and acetic acid) were distilled into the Dean-Stark trap (135-146° C.). Distillation was continued for another hour, during which the pot temperature slowly rose to 190° C. and the distillate slowed to a trickle to drive over any more solvent. Approximately 250 ml of solvent was collected. The residue was cooled below 100° C. and dioxane was added.

A 2N sodium hydroxide (222.85 ml, 0.4457 mol) and 8-aminocaprylic acid (70.96 g, 0.4457 mol) solution was added to the solution of oligo(5-chloroasalicylic acid) (0.5794 mol) in dioxane. The reaction mixture was heated to 90° C. for 5.5 hours, then shut off overnight and restarted in the morning to heat to reflux (after restarting the heating the reaction was monitored at which time the reaction was determined to have finished, by HPLC). The reaction mixture was cooled to 40° C. The dioxane was stripped off in vacuo. The residue was taken up in 2N sodium hydroxide and acidified. The material did not solidify. The material was then taken up in ethyl acetate and extracted (2×100 ml) to remove excess dioxane. The ethyl acetate layer was dried over sodium sulfate and concentrated in vacuo. The easily filtered solids were collected by filtration. The remaining material was taken up in 2N NaOH. The pH was adjusted to 4.3 to selectively isolate product from starting material. Once at pH 4.3, the solids were filtered off and recrystallized in a 1:1 mixture of ethanol and water. Any insoluble material was hot filtered out first. All the solids which were collected were combined and recrystallized from the mixture of ethanol and water to give 52.06 g of the free acid product as a white solid.

The sodium salt solution was prepared according to the method described in Example 19 using 0.2 N NaOH solution. Percent purity was calculated to be 100% using 0.5038 g of 5-CNAC and 16.06 ml of 0.2 N NaOH. The sodium salt solution was prepared using 250 ml of 0.2 N NaOH and 9.4585 g of 5-CNAC prepared as described above. The solution was filtered through a 0.45 micron filter.

Example 21

Oral Delivery of sCT/Sodium Salt of 5-CNAC in Rats

Male Sprague-Dawley rats weighing between 200-250 g were fasted for 24 hours and were administered ketamine (44 mg/kg) and chlorpromazine (1.5 mg/kg) 15 minutes prior to dosing. The rats were administered one of the following:

(4a) orally, one capsule of 13 mg lyophilized powder as prepared as in Example 19 with 0.5 ml of water to flush the capsule down;

(4b) orally, 1.0 ml/kg of a reconstituted aqueous solution of the lyophilized powder prepared in Example 19;

(4c) orally, 1.0 ml/kg of "fresh", unlyophilized aqueous solution of 5-CNAC sodium salt as prepared in Example 20 with sCT; or (4d) subcutaneously, 5 mg/kg of sCT.

Doses (4a), (4b) and (4c) contained 50 mg/kg of the sodium salt of 5-CNAC and 100 mg/kg of sCT. Doses for (4a) are approximate because the animals were given one capsule filled with the stated amount of powder based on an average animal weight of 250 g, whereas actual animal weight varied. This is also the case in all later examples where a capsule is dosed.

The reconstituted solution for (4b) was prepared by mixing 150 mg of the lyophilized powder prepared as in Example 19 in 3 ml of water. The reconstituted solution was dosed at 1.0 ml/mg.

The "fresh" solution for (4c) was prepared from unlyophilized material using 150 mg 5-CNAC sodium salt prepared in Example 20 in 3 ml water plus 150 ml of sCT stock solution (2000 ml/ml prepared in 0.1M phosphate buffer, pH adjusted to 4 with HCl and NaOH. The "fresh" solution had a final concentration of 50 mg/ml 5-CNAC sodium salt and of 100 mg/ml sCT, and 1.0 ml/kg was dosed.

The subcutaneous doses were prepared by dissolving 2 mg of sCT in 1 ml water. 5 mL of this solution was added to 995 mL of water. This solution was dosed at 0.5 ml/kg.

Blood samples were collected serially from the tail artery. Serum sCT was determined by testing with an EIA kit (Kit #EIAS-6003 from Peninsula Laboratories, Inc., San Carlos, Calif.), modifying the standard protocol from the kit as follows: incubated with 50 ml peptide antibody for 2 hours with shaking in the dark, washed the plate, added serum and biotinylated peptide and diluted with 4 ml buffer, and shook overnight in the dark. Results are illustrated in Table 5, below.

TABLE 5

Oral Delivery of sCT/Sodium Salt of 5-CNAC in Rats

| Dosage form | Dose of Sodium Salt of 5-CNAC (mg/kg) | sCT Dose (mg/kg) | Mean Peak Serum sCT ± SD (pg/ml) |
| --- | --- | --- | --- |
| (4a) capsule | 50* | 100* | 1449 ± 2307 |
| (4b) reconstituted solution | 50 | 100 | 257 ± 326 |
| (4c) unlyophilized solution | 50 | 100 | 134 ± 169 |
| (4d) subcutaneous | — | 5 | 965 ± 848 |

*approximate dose due to variations in animal weight

Example 22

Oral Delivery of sCT/Sodium Salt of 5-CNAC in Rats

According to the method described in Example 21, rats were administered one of the following:

(5a) orally, one capsule of 13 mg lyophilized powder with 1 ml water to flush the capsule down;

(5b) orally, one capsule of 6.5 mg lyophilized powder with 1 ml water to flush the capsule down;

(5c) orally, one capsule of 3.25 mg lyophilized powder with 1 ml water to flush the capsule down;

(5d) subcutaneously 5 mg/kg of sCT.

Approximate amounts of delivery agent and sCT, as well as the results, are shown in Table 6 below.

TABLE 6

Oral Delivery of sCT/Sodium Salt of 5-CNAC in Rats

| Dosage form | Dose of Sodium Salt of 5-CNAC (mg/kg) | sCT Dose (mg/kg) | Mean Peak Serum sCT ± SD (pg/ml) |
|---|---|---|---|
| (5a) capsule | 50* | 100* | 379 ± 456 |
| (5b) capsule | 25* | 50* | 168 ± 241 |
| (5c) capsule | 12.5* | 25* | 0 |
| (5d) subcutaneous | — | 5 | 273 ± 320 |

*approximate dose due to variations in animal weight

Example 23

Preparation of N-(5-chlorosalicyloyl)-4 aminobutyric acid

Sodium carbonate (30 g, 0.2835 mol) was added to a 500 ml 3-neck, round-bottomed flask containing 6-chloro-2H-1,3-benzoxazine-2,4(3H)-dione (prepared as in Example 18) (50 g, 0.2532 mol) and dimethylacetamide (75 ml) and stirred. Methyl-4-bromobutyrate (45.83 g, 0.2532 mol) was added in one portion to the stirring reaction mixture, and heating of the reaction mixture was started. The reaction temperature was maintained at 70° C. and allowed to heat overnight. Heating was discontinued, and the reaction mixture was allowed to cool to room temperature.

The reaction mixture was vacuum filtered and the filter cake was washed with ethyl alcohol. The filter cake and filtrate were monitored by HPLC to determine where the product was. Most of the product was washed into the filtrate, although some product was still present in the filter cake. The filter cake was worked up to recover product to increase the final yield. The filter cake was washed first with copious amounts of water, then with ethyl acetate. The washes from the filter cake were separated and the ethyl acetate layer was next washed twice with water, once with brine, then dried over sodium sulfate, isolated and concentrated in vacuo to recover more solids (solids B). Water was added to the filtrate that had been isolated earlier and solids precipitated out. Those solids were isolated (solids A). Solids A and B were combined and transferred to a round bottom flask and 2N NaOH was added to the filtrate and heating was begun with stirring. The reaction was monitored by HPLC to determine when the reaction was done. The reaction was cooled to 25° C., stirred overnight, and concentrated in vacuo to remove excess ethanol. An ice/water bath was placed around the reaction vessel and the slurry was acidified. The solids were recovered by vacuum filtration and the filter cake was washed with water, dried and sent for NMR analysis.

The solids were isolated and transferred to an Erlenmeyer flask to be recrystallized. The solids were recrystallized with methanol/water. Solids formed and were washed into a Buchner funnel. More solids precipitated out in the filtrate and were recovered. The first solids recovered after recrystallization had formed a methyl ester. All the solids were combined, 2N NaOH was added and heated again to reflux to regain the free acid. Once the ester had disappeared, as determined by HPLC, acidification of the mixture to a pH of about 4.7 caused solids to develop.

The solids were isolated by filtration and combined with all the solids and recrystallized using a 1.5:1.0 ratio of methanol to water. White solids precipitated out overnight and were isolated and dried to give 23.48 g of N-(5-chlorosalicyloyl)-4 aminobutyric acid at a 36% yield.

It was later determined that the filter cake should have first been washed with excess ethyl alcohol to avoid having the product remain in the filter cake. From that point, the filtrate and 2N NaOH could be heated with stirring, cooled to 25° C. and concentrated in vacuo to remove excess ethanol. In an ice/water bath, the slurry acidified to a pH of 4.7. The solids recovered by vacuum filtration and the filter cake were washed with water. The solids were then isolated and recrystallized.

Example 24

Lyophilization of sCT/Sodium Salt of N-(5-chlorosalicyloyl)-4 aminobutyric acid

Following the procedure in Example 19, a lyophilized powder of sCT/sodium salt of N-(5-chlorosalicyloyl)-4 aminobutyric acid was prepared and packed into capsules. 10.528 g of N-(5-chlorosalicyloyl)-4 aminobutyric acid as prepared in Example 23 was dissolved in 150 ml water. 4.72 ml 10N NaOH was added. 21.0566 mg of sCT was dissolved in 10 ml phosphate buffer and the sCT/phosphate buffer mixture was added to the delivery agent solution. Water was added to make the volume 250 ml.

Example 25

Oral Delivery of sCT/Sodium Salt of N-(5-chlorosalicyloyl)-4 aminobutyric acid in Rats According to the method of Example 21, with the exception that the standard protocol for the EIA kit was followed, rats were administered orally one capsule of 13 mg lyophilized powder with 0.5 ml water to flush the capsule down with the approximate amounts of the sodium salt of N-(5-chlorosalicyloyl)-4 aminobutyric acid and sCT as set forth in Table 7 below. The results are also shown in Table 7.

TABLE 7

Oral Delivery of sCT/Sodium Salt of N-(5-chlorosalicyloyl)-4 aminobutyric acid in Rats

| Dosage form | Dose of Sodium Salt of N-(5-chlorosalicyloyl)-4 aminobutyric acid (mg/kg) | sCT Dose (mg/kg) | Mean Peak Serum sCT ± SD (pg/ml) |
|---|---|---|---|
| (8a) capsule | 50* | 400* | 1112 ± 1398 |
| (8b) capsule | 50* | 800* | 2199 ± 4616 |

*approximate dose due to variations in animal weight

Example 26

Preparation of 5-CNAC for Tableting

To a clean, dry, 200 gallon glass-lined reactor, 178 L of dry acetonitrile was added. The agitator was set to 100-125 RPM and the reactor contents were cooled to 9° C. 74 kg of 5-chloro salicylamide, available from Polycarbon Industries of Leominster, Mass., was charged to the reactor and the charging port was closed. 47 L of dry pyridine was charged to the reactor. The slurry was cooled to 9° C. prior to proceeding. Cooling was applied to the reactor condenser and valve overheads were set for total reflux. Over 2 hours, 49.7 kg of ethylchloroformate was charged to the 200 gallon reactor while maintaining the batch temperature at 14° C. Note that ethylchloroformate can contain 0.1% phosgene and is extremely reactive with water. The reaction is highly exothermic and requires the use of a process chiller to moderate reaction temperature. The reactor contents were agitated for 30 minutes at 10-14° C. once the ethylchloroformate addition was complete. The reactor contents were heated to 85° C. over 25 minutes, collecting all distillate into a receiver. The reactor contents were held at 85-94° C. for approximately 6 hours, collecting all distilled material into a receiver. The reaction mixture was sampled and the conversion (>90%) monitored by HPLC. The conversion was found to be 99.9% after 6 hours. The reactor contents were cooled to 19° C. over a one-hour period. 134 L of deionized water was charged to the reactor. A precipitate formed immediately. The reactor contents were cooled to 5° C. and agitated for 10.5 hours. The product continued to crystallize out of solution. The reactor slurry was centrifuged. 55 L of deionized water was charged to the 200-gallon, glass-lined reactor and the centrifuge wet cake was washed. The intermediate was dried under full vacuum (28" Hg) and 58° C. for 19.5 hours. The yield was 82.6 kg 6-chloro-2H-1,3-benzoxazine-2,4(3H)-dione. This intermediate was packaged and stored so that it was not exposed to water.

In the next preparation, absolutely no water can be tolerated in the steps up to the point where distilled water is added.

222 L of dry dimethylacetamide was charged to a dry 200 gallon glass-lined reactor. The reactor agitator was set to 100-125 RPM. Cooling was applied to the condenser and valve reactor overheads were set for distillation. 41.6 kg of dry anhydrous sodium carbonate was charged to the reactor and the reactor charging port was closed. Caution was used due to some off-gassing and a slight exotherm. 77.5 kg of dry 6-chloro-2H-1,3-benzoxazine-2,4(3H)-dione was charged to the reactor. Quickly, 88 kg of dry ethyl-8-bromooctanoate was charged to the reactor. 22-24 inches of vacuum was applied and the reactor temperature was raised to 65-75° C. The reactor temperature was maintained and the contents were watched for foaming. The reactor mixture was sampled and monitored for conversion by monitoring for the disappearance of the bromo ester in the reaction mixture by gas chromatography (GC). The reaction was complete (0.6% bromo ester was found) after 7 hours. The vacuum was broken and the reactor contents cooled to 45-50° C. The contents were centrifuged and the filtrate sent into a second 200-gallon glass-lined reactor. 119 L of ethanol (200 proof denatured with 0.5% toluene) was charged to the first 200-gallon reactor, warmed to 45° C. and the filter cake washed with warm ethanol, adding to the reaction mixture in the second 200-gallon reactor. The agitator was started on the second 200-gallon reactor. The reactor contents were cooled to 29° C. 120 L of distilled water was slowly charged to the second reactor, with the water falling directly into the batch. The reactor contents were cooled to 8° C. The intermediate came out of solution and was held for 9.5 hours. The resultant slurry was centrifuged. 70 L of ethanol was charged to the reactor, cooled to 8° C. and the centrifuge cake was washed. The wet cake was unloaded into double polyethylene bags placed inside a paper lined drum. The yield was 123.5 kg of ethyl 8-(6-chloro-2H-1,3-benzoxazine-2,4(3H)-dionyl)octanoate.

400 L of purified water, USP and 45.4 kg NaOH pellets were charged to a 200 gallon glass-lined reactor and the agitator was set to 100-125 RPM. 123.5 kg of the ethyl 8-(6-chloro-2H-1,3-benzoxazine-2,4(3H)-dionyl)octanoate wet cake was charged to the reactor. The charging port was closed. Cooling water applied to the condenser and the valve reactor overheads were set for atmospheric distillation. The reactor contents were heated to 98° C. and conversion monitored by HPLC. Initially (approximately 40 minutes) the reactor refluxed at 68° C., however, as the ethanol was removed (over 3 hours) by distillation the reactor temperature rose to 98° C. The starting material disappeared, as determined by HPLC, at approximately 4 hours. The reactor contents were cooled to 27° C. 150 L of purified water and USP were charged to an adjacent 200 gallon glass-lined reactor and the agitator was set to 100-125 RPM. 104 L of concentrated (12M) hydrochloric acid was charged to the reactor and cooled to 24° C. The saponified reaction mixture was slowly (over 5 hours) charged to the 200-gallon glass-lined reactor. The material (45 L and 45 L) was split into 2 reactors (200 gallons each) because of carbon dioxide evolution. The product precipitated out of solution. The reaction mixture was adjusted to a pH of 2.0-4.0 with 50% NaOH solution (2 L water, 2 kg NaOH). The reactor contents were cooled to 9-15° C. The intermediate crystallized out of solution over approximately 9 hours. The reactor slurry was centrifuged to isolate the intermediate. 50 L of purified water and USP were charged to a 200-gallon glass-lined reactor and this rinse was used to wash the centrifuge wet cake. The wet cake was unloaded into double polyethylene bags placed inside a plastic drum. The N-(5-chlorosalicyloyl)-8-aminocaprylic acid was dried under vacuum (27" Hg) at 68° C. for 38 hours. The dry cake was unloaded into double polyethylene bags placed inside a 55-gallon, steel unlined, open-head drums with a desiccant bag placed on top. The dried isolated yield was 81 kg of N-(5-chlorosalicyloyl)-8-aminocaprylic acid.

Example 27

Lyophilization of sCT/Sodium Salt of 5-CNAC for Tableting

The method of Example 19 was used to prepare lyophilized powder using 200 g of 5-CNAC as prepared in Example 26. The NaOH solution was made by dissolving 42 g of 100% NaOH into 2000 ml water. The slurry was stirred at room temperature, and vacuum filtered over a 0.45 micron filter. The pH of the solution containing the sodium salt of 5-CNAC was about 8.6. 200 mg of sCT was used.

Example 28

Preparation of sCT/Sodium Salt of 5-CNAC Tablets

Tablets of the lyophilized powder prepared in Example 27 were prepared as follows.

An instrumented Carver press (Model C), available from Carver of Wabash, Ind., was used for tablet compression. The die used was 0.245" in diameter. The top punch was flat-faced, bevel-edged and 0.245" in diameter while the bottom punch was flat-faced, scored, bevel-edged and 0.245" in diameter. The press was capable of measuring the upper and lower punch force as well as the displacement of the upper punch. A formula for direct compression was designed as shown in Table 8 below:

TABLE 8

| Material | mg/tablet | mg/300 tablet batch |
|---|---|---|
| Lyophilized powder of sCT/sodium salt of 5-CNAC | 100.2 | 30,060.0 |
| AC-DI-SOL ® | 2.004 | 601.2 |

TABLE 8-continued

| Material | mg/tablet | mg/300 tablet batch |
|---|---|---|
| Magnesium Stearate | 0.511 | 153.3 |
| CAB-O-SIL ® | 0.205 | 61.5 |
| Total Weight (mg) | 102.92 | 30,876.0 |

AC-DI-SOL ® is croscarmellose sodium (NF, PH.Eur., JPE) and is available from FMC Corporation, Pharmaceutical Division, of Philadelphia, PA.
CAB-O-SIL ® is fumed silica and is available from Cabot Corporation, Tuscola, IL.

The Ac-Di-Sol® and Cab-O-Sil® were weighed and transferred to a mixing bottle. The bottle was then closed and secured to the arm of a sustained release apparatus set at 25 rotations per minute (RPM). The apparatus was rotated for 5 minutes to mix. The lyophilized powder of 5-CNAC/sCT was then added to the AC-DI-SOL®/CAB-O-SIL® mixture geometrically with a two minute mixing cycle after each addition. Magnesium stearate was then added to the above mixture and mixing was continued for five minutes.

Approximately 103 mg of the above powder was then transferred to the die containing the lower punch. The powder was pressed down into the die using the upper punch. The upper punch was inserted and the punch die assembly was mounted onto the press. Compression was then performed. The upper punch was used to push the tablet out of the die.

Example 29

Oral Delivery of sCT/Sodium Salt of 5-CNAC in Rats

Tablets

The tablets prepared in Example 28 were pulverized and hand packed into capsules at 13 mg/capsule. Untableted, lyophilized powder as prepared in Example 27 was hand packed into capsules at 13 mg/capsule. The capsules were dosed with 1 ml water to flush them down.

Following the procedure of Example 21, with the exception that the standard protocol for the EIA kit was followed instead of the modified version, rats were administered orally one capsule with 1 ml of water to flush the capsule down with the approximate amounts of sodium salt of 5-CNAC and sCT as set forth in Table 9 below. The results are also shown in Table 9.

TABLE 9

Oral Delivery of sCT/Sodium Salt of 5-CNAC in Rats

| Dosage form | Dose of Sodium Salt of 5-CNAC (mg/kg) | sCT Dose (mg/kg) | Mean Peak Serum sCT ± SD (pg/ml) |
|---|---|---|---|
| (12a) tableted powder in capsule | 50* | 100* | 198 ± 132 |
| (12b) untableted powder in capsule | 50* | 100* | 197 ± 125 |

*approximate dose due to variations in animal weight

Example 30

Preparation of 5-CNAC

5-CNAC was made under similar conditions as in Example 26 in a laboratory environment.

Example 31

Lyophilization of sCT/Sodium Salt of 5-CNAC

5-CNAC as prepared in Example 30 was formulated into a lyophilized powder with sCT as in Example 19 with 485 ml 0.2 N NaOH and 19.0072 g of 5-CNAC in a steam bath. The final volume was 505 ml. Four separate batches were prepared from 187, 138, 74 and 160 ml of the sodium salt 5-CNAC with 28, 48, 40 and 360 mg sCT, respectively. The estimated amounts of the sodium salt of 5-CNAC were 7, 5, 2.5 and 4.5 g, respectively.

Example 32

Oral Delivery of sCT/Sodium Salt of 5-CNAC in Rats

According to the method of Example 21, with the exception that the standard protocol for the EIA kit was followed instead of the modified version, rats were administered orally one capsule of 13 mg lyophilized powder using one of the four batches prepared in Example 31, with 1 ml water to flush the capsule down. The approximate amounts of the sodium salt of 5-CNAC and sCT are set forth in Table 10 below. The results are shown in Table 10.

TABLE 10

Oral Delivery of sCT/Sodium Salt of 5-CNAC in Rats

| Dosage form | Dose of Sodium Salt of 5-CNAC (mg/kg) | sCT Dose (mg/kg) | Mean Peak Serum sCT ± SD (pg/ml) |
|---|---|---|---|
| (15a) capsule | 50* | 100* | 125 ± 153 |
| (15b) capsule | 50* | 400* | 178 ± 354 |
| (15c) capsule | 50* | 800* | 546 ± 586 |
| (15d) capsule | 50* | 4000* | 757 ± 1234 |

*approximate dose due to variations in animal weight

All patents, publications, applications, and test methods mentioned above are hereby incorporated by reference. Many variations of the present matter will suggest themselves to those skilled in the art in light of the above detailed description. All such obvious variations are within the patented scope of the appended claims.

What is claimed is:

1. A composition comprising about 50% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

2. The composition of claim 1, wherein the composition comprises about 60% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

3. The composition of claim 1, wherein the composition comprises about 70% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

4. The composition of claim 1, wherein the composition comprises about 80% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

5. The composition of claim 1, wherein the composition comprises about 90% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

6. The composition of claim 1, wherein the composition comprises about 96% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

7. The composition of claim 1, wherein the composition comprises about 98% or more by weight of the disodium salt of N-(5-chlorosalicyloyl)-8-aminocaprylic acid, based upon 100% total weight of N-(5-chlorosalicyloyl)-aminocaprylic acid and salts thereof in the composition.

8. The composition form of claim 1, wherein the composition comprises from about 50% to about 90% by weight of the disodium salt of N-(5-chlorosalicyloyl)-8-aminocaprylic acid, based upon 100% total weight of N-(5-chlorosalicyloyl)-aminocaprylic acid and salts thereof in the composition.

9. The composition of claim 1, wherein the composition comprises from about 50% to about 96% by weight of the disodium salt of N-(5-chlorosalicyloyl)-8-aminocaprylic acid, based upon 100% total weight of N-(5-chlorosalicyloyl)-aminocaprylic acid and salts thereof in the composition.

10. The composition of claim 1, wherein the disodium salt is in a monohydrate form.

11. The composition of claim 1, wherein the disodium salt is anhydrous.

12. The composition of claim 1, wherein the composition is in the form of an oral dosage form.

13. The composition of claim 1, wherein the composition is in the form of a tablet.

14. The composition of claim 1, wherein the composition is in the form of a capsules.

* * * * *